United States Patent

Stein et al.

Patent Number: 5,342,870
Date of Patent: Aug. 30, 1994

[54] ADDITION-CURABLE SILICONE ADHESIVE COMPOSITIONS, AND BIS(TRIALKOXYSILYLALKYLENEOXY-CARBONYLALKYLENE) AMINE ADHESION PROMOTERS

[75] Inventors: Judith Stein; Joseph A. King, Jr.; Andrew J. Caruso, all of Schenectady, N.Y.

[73] Assignee: General Electric Company, Schenectady, N.Y.

[21] Appl. No.: 166,853

[22] Filed: Dec. 15, 1993

[51] Int. Cl.$^5$ .............. C08K 5/54; C07F 7/04
[52] U.S. Cl. .................. 524/188; 524/262; 524/588; 525/478; 528/15; 528/31; 528/32; 556/418
[58] Field of Search .............. 524/188, 262, 588; 525/478; 528/15, 31, 32; 556/418

[56] References Cited

U.S. PATENT DOCUMENTS

| | | | |
|---|---|---|---|
| 4,087,585 | 5/1978 | Schulz | 428/429 |
| 4,332,844 | 6/1982 | Hamada et al. | 427/387 |
| 4,753,978 | 6/1988 | Jensen | 525/478 |
| 4,980,413 | 12/1990 | Kasuya | 524/730 |
| 5,164,461 | 11/1992 | Mitchell et al. | 525/478 |
| 5,173,529 | 12/1992 | Fujiki et al. | 524/188 |

FOREIGN PATENT DOCUMENTS 2116575  9/1983  United Kingdom ............ 556/418

OTHER PUBLICATIONS

Abstract—Adhesive Siloxane Compositions, Fujiki et al—Application: EP 91-304524, May 20, 1991; Priority: JP 90-138607, May 30, 1990—(1 page).
Abstract—Organopolysiloxane-based Adhesive Compositions—Fujiki et al—Application: EP 91304524; Priority JP 90138607 (no date)—(1 page).

Primary Examiner—John C. Bleutge
Assistant Examiner—Mark D. Sweet
Attorney, Agent, or Firm—William A. Teoli; William H. Pittman

[57] ABSTRACT

Addition-curable platinum group metal catalyzed silicone compositions are provided which utilize a bis(-trialkoxysilylalkyleneoxycarbonylalkylene)amine adhesion promoter, such as $NH[CH_2CH_2C(O)OCH_2CH_2CH_2Si(OCH_3)_3]_2$. Cohesive bonding is effected on both plastic and metal substrates at temperatures of 100° C. or less and in 1 hour or less.

7 Claims, No Drawings

ADDITION-CURABLE SILICONE ADHESIVE COMPOSITIONS, AND BIS(TRIALKOXYSILYLALKYLENEOXY-CARBONYLALKYLENE) AMINE ADHESION PROMOTERS

BACKGROUND OF THE INVENTION

The present invention relates to platinum group metal catalyzed addition-curable silicone adhesive compositions employing a bis(trialkoxysilylalkyleneoxycarbonylalkylene)amine as an adhesion promoter.

As shown by Schulz U.S. Pat. No. 4,087,585, some self adhering silicone compositions which cure at temperatures of about 150° C., employ an adhesion promoter which is made by mixing a moisture sensitive epoxy containing silane and a hydroxylated vinyl containing polysiloxane under anhydrous conditions. Although many of the adhesion promoters used in addition-curable silicone adhesive compositions do not require special mixing conditions, many of the available adhesion promoters do not provide addition-curable silicone adhesive compositions having a satisfactory degree of adhesion to both metallic and thermoplastic substrates. In determining whether the degree of adhesion on a substrate is satisfactory, the adhesive composition can be applied onto the substrate, such as plastic or metal and thereafter cured. It would be desirable to produce a silicone-substrate composite having a silicone layer which failed cohesively instead of adhesively when tested. As used hereinafter, the expression "adhesive failure" means the silicone layer can be cleanly separated from the substrate, while in a "cohesive failure", rupture occurs in the silicone layer, or in the substrate when separation is achieved.

SUMMARY OF THE INVENTION

The present invention is based on the discovery that certain bis(silylalkylene)amines, such as a bis(trialkoxysilylalkyleneoxycarbonylalkylene) amine, have been found to be effective as adhesion promoters when used in a platinum group metal catalyzed addition-curable silicone composition, as defined hereinafter. In addition, the resulting curable composition, has been found to provide a silicone adhesive which can be cured at a temperature at or below 100° C. and in less than 1 hour. In addition, a cohesive bond can be formed when cured in contact with a plastic or metallic substrate.

STATEMENT OF THE INVENTION

There is provided by the present invention, a platinum group metal catalyzed addition-curable silicone composition, comprising by weight, (A) 100 parts of a vinyl-containing polydiorganosiloxane composition comprising, (1) about 50 to about 100 parts of an essentially cyclic-free vinyl-terminated polydiorganosiloxane having the general formula,

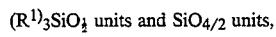  (1)

where $V_i$ is a vinyl radical, R is selected from the class consisting of alkyl radicals having 1 to 8 carbon atoms, phenyl radicals, fluoroalkyl radicals having 3 to 10 carbon atoms and mixtures thereof, "m+n" has a value sufficient to provide a polydiorganosiloxane having viscosity of 100 to about 100,000 centipoise at 25° C., and a vinyl content of from about 0.02 to about 2.0 weight %, and (2) from about 0 to about 50 parts of a solid, benzene-soluble vinyl-containing resin copolymer comprising, $(R^1)_3SiO_{\frac{1}{2}}$ units and $SiO_{4/2}$ units, where $R^1$ is a vinyl radical, or a monovalent hydrocarbon radical free of aliphatic unsaturation and containing no more than six carbon atoms, the ratio of $(R^1)_3 SiO_{\frac{1}{2}}$ units to $SiO_{4/2}$ units being from about 0.5:1 to about 1.5:1, and the vinyl-containing resin having a vinyl content of from about 1.5 to about 3.5% by weight, (B) from about 1 to about 20 parts of a hydrogen-containing polysiloxane having an average unit formula, $$R^2{}_aH_bSiO_{(4-a-b)/2},$$  (2)

where $R^2$ is a monovalent hydrocarbon radical, or halogenated monovalent hydrocarbon radical having from 1 to about 10 carbon atoms and free of aliphatic unsaturation, "a" has a value of from about 0 to about 3, "b" has a value of from about 0 to about 3, and the sum of "a"+"b" has a value of from 0 to 3, (C) a catalytic amount of a platinum group metal hydrosilylation catalyst, (D) an effective amount of a bis(trialkoxysilylalkyleneoxycarbonylalkylene)amine, having the formula,, $$NH[R^3C(O)OR^4Si(OR^5)_3]_2$$  (3)

where $R^3$ and $R^4$ are selected from the same or different $C_{(2-8)}$ alkylene radicals, and $R^5$ is selected from the same or different $C_{(1-4)}$ alkyl radical.

(E) from about 0 to about 200 parts of an extending filler, and (F) from about 0 to about 50 parts of a reinforcing filler, and in the absence of (A)(2), an amount effective for reinforcement.

In a further aspect of the present invention, there are provided bis(trialkoxysilylalkyleneoxycarbonylalkylene)amines of formula (3) referred to hereinafter as "adhesion promoters",and method for making. A preferred procedure for making the adhesion promoters of of formula (3) is by effecting reaction at a temperature of 0° C. to about 100° C. between an alkenoyloxyalkylenepolyalkoxysilane, such as 3acryloyloxypropyltrimethoxysilane, and an organic aromatic alkylamine such as benzylamine. The resulting product can be debenzylated in a hydrogenation apparatus at a pressure of about 10 psi to about 100 psi and at a temperature of 0° C. to 50° C.

The addition curable compositions of the present invention can be used as adhesives in industrial multi-layered laminates. These adhesives also can adhere to substrates that are in contact with the compositions during curing. Substrates which are included are glass, metals, metal oxides, and plastics. Among the plastics, there are included, polyetherimides, phenolic resins, epoxy resins, polyamides, unsaturated polyesters, poly (ethylene terephthalate), polycarbonates, polyphenylene sulfide, polyacetals, and polyimides.

There are included within the"adhesion promoters" of formula (3) compounds such as,

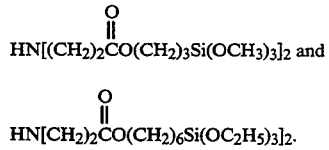

An effective amount of the adhesion promoter is 0.6 to 2.0 parts by weight of adhesion promoter, per 100 parts by weight of the platinum group metal catalyzed addition-curable adhesion composition, referred to hereinafter as the "addition-curable composition".

The vinyl-terminated polydiorganosiloxane of formula (1) preferably has a viscosity of from about 3000 to about 95,000 centipoise at 25° C. Radicals represented by R are preferably alkyl radicals of 1 to about 4 carbon atoms, and most preferably methyl.

Component (A) (2) is a vinyl-containing benzene-soluble siloxane resin containing $(R^1)_3SiO_{\frac{1}{2}}$ units, or (M units), and $SiO_{4/2}$ units, or (Q units), wherein each $R^1$ is a vinyl radical, or a monovalent hydrocarbon radical free of aliphatic unsaturation and containing no more than six carbon atoms, the ratio of $(R^1)_3SiO_{\frac{1}{2}}$ units to $SiO_{4/2}$ units being from about 0.5:1 to about 1.5:1, the resin having a vinyl content of from about 1.5 to about 3.5% by weight. Component (A) (2) also is referred to as the "vinyl- containing MQ resin".

Component (A) (2) may further contain (i) $R^1SiO_{3/2}$ units, (ii) $(R^1)_2SiO_1$ units, or both (i) and (ii), the $(R^1)_2SiO_1$ units being present in an amount equal to from about 0 to about 10 mole percent based on the total number of moles of siloxane units in (A) (2), and the $R^1SiO_{3/2}$ units being present in an amount equal to from about 0 to about 10 mole percent based on the total number of moles of siloxane units in (A) (2).

Component (A) comprises from about 50 to about 100, and preferably from about 56 to about 100, and most preferably from about 60 to about 75, parts by weight of (A) (1) and from about 0 to about 50, preferably from about 0 to about 40, and most preferably from about 25 to about 40, parts by weight of (A) (2).

In one preferred embodiment of the composition of the present invention, component (A) comprises from about 60 to about 75 parts by weight of (1) a vinyl terminated polydiorganosiloxane having a viscosity of 65,000 to about 95,000 centipoise at 25° C., and (2) from about 25 to about 40 parts by weight of the vinyl-containing MQ resin.

In another preferred embodiment of the composition of the present invention, component (A) comprises from about 60 to about 75 parts by weight of (1) a vinyl terminated polydiorganosiloxane having a viscosity of 3000 to about 5000 centipoise at 25° C., and (2) from about 25 to about 40 parts by weight of the vinyl-containing MQ resin.

In a further preferred embodiment of the composition of the present invention, component (A) comprises 100 parts by weight of:
  (1) a blend containing from about 25 to about 35 parts by weight of the vinyl-containing polydiorganosiloxane of formula (1) having a viscosity of 3000 to about 5000 centipoise of 25° C. and from about 65 to about 75 parts by weight of a vinyl-containing polydiorganosiloxane of formula (1) above and having a viscosity of 75,000 to about 95,000 centipoise at 25° C., the total amount of (1) being 100 parts by weight. Preferably, component (A) will additionally contain,
  (2) from about 5.5 to about 7.5 parts by weight of a low viscosity polydiorganosiloxane composition having an average of at least one vinyldiorganosiloxy end group, a vinyl content of from about 0.2 to about 0.3% by weight and a viscosity of from about 400 to about 700 centipoise at 25° C.,
  (3) from about 5.5 to about 7.5 parts by weight of a low viscosity vinyldiorgano end-stopped, diorganopolysiloxane having a vinyl content of from about 1.4 to about 2.0% by weight and a viscosity of from about 300 to about 600 centipoise at 25° C. and free of the vinyl containing MQ resin. Preferably, reinforcing filler in present in the composition containing (A)–(E), if (A) contains this vinyl polymer blend.

The hydrogen-containing polysiloxane of formula (2) functions as a crosslinking agent. A preferred hydrogen containing polysiloxane has the formula,

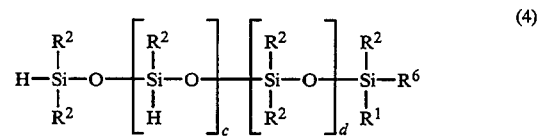

(4)

wherein $R^2$ is as defined above, $R^6$ is $R^2$ or hydrogen, "c" and "d" have values which are sufficient when added together to provide a viscosity of from about 10 to about 1000, and as a hydrogen containing polysiloxane fluid, has a hydrogen content of from about 0.02 to about 1.6% by weight.

The hydrogen-containing polysiloxane fluid of formula (4), can be used as a hydride cross-linking agent in the present invention. In formulas (2) and (4) above, $R^2$ is preferably selected from alkyl radicals of 1 to 8 carbon atoms, phenyl, fluoroalkyl radicals of 3 to 10 carbon atoms and hydrogen, the preferred fluoroalkyl radical being trifluoropropyl. Most preferably, $R^2$ represents a methyl radical.

The hydrogen-containing polysiloxane fluid of formula (4) can have a viscosity of from about 10 to about 1000 and preferably from about 10 to about 150 centipoise at 25° C.

Other hydrogen-containing polysiloxane fluids which can be used in the present invention include fluid siloxane copolymer resins comprised of $(R^1)_3SiO_{\frac{1}{2}}$ ("M") units, $SiO_{4/2}$ ("Q") units, and units such as $H(R_2)_2SiO_{\frac{1}{2}}$ ("$M^H$"), $HR^2SiO_1$ ("$D^H$") and $(R^2)_2SiO_1$ ("D") and mixtures of fluid polyorganosiloxanes and fluid siloxane copolymer resins described in U.S. Pat. No. 3,627,851, which is hereby incorporated by reference herein. The preferred resins are known as $M^HQ$ resins, which comprise diorganohydrogensiloxy units ($M^H$) units and $SiO_{4/2}$ (Q) units, wherein the ratio of diorganohydrogensiloxy units ($M^H$) units to Q units is from 0.4:1.0 to 2.0:1.00 inclusive. Hydrogen containing polysiloxanes having at least one $R^1$ group, preferably, a methyl group, bonded to silicon which bears at least one reactive hydrogen atom are preferred. It is to be understood that the hydrogen containing polysiloxane can be a single compound or a mixture of compounds. Additional hydrogen containing polysiloxanes suitable for use in the present invention are disclosed, for example, in U.S. Pat No. 4,061,609 to Bobear, which is hereby incorporated by reference herein.

Further examples of hydrogen-containing polysiloxanes which can be used in the present invention are linear triorgano-endstopped organohydrogenpolysiloxane fluids having a viscosity of from about 15 to about 40 centistokes at 25° C., and a hydrogen content of 1.6% by weight. These hydrogen containing polysiloxanes generally have the formula,

wherein $R^2$ is as previously defined herein and "e" is a number sufficient to provide a viscosity of from about 15 to about 40 centistokes at 25° C.

It is preferred that the hydrogen-containing polysiloxane of formulas (4) and (5) have a hydride content of 0.05 to 1.6%, and more preferably of 0.1 to 1% by weight. In instances where the vinyl containing polydiorganopolysiloxane of formula (1) has a viscosity of between 3000 to 5000 centipoise and the hydrogen containing polysiloxane is a triorganostopped organohydrogensiloxane, the SiH:SiVinyl ratio is preferably at least 2.1:1, while about 2.1:1 to about 10.1, or from about 2.1:1 to about 3.5:1 is particularly preferred.

Component (C) of the adhesion composition of the present invention which promotes the hydrosilylation reaction is a platinum group metal catalyst. Additional catalysts for facilitating the hydrosilylation curing reaction include precious metal catalysts such as those which use ruthenium, rhodium, palladium, osmium, and iridium, and complexes of these metals. Examples of suitable hydrosilylation catalysts for use in the present invention are disclosed, for example in U.S. Pat. Nos. 3,159,601 and 3,159,662 (Ashby); U.S. Pat. No. 3,220,970 (Lamoreaux); U.S. Pat. No. 3,775,452 (Karstedt); U.S. Pat. No. 3,516,946 (Modic), and U.S. Pat. No. 4,029,629 (Jeram); all of the foregoing patents being hereby incorporated by reference herein.

Preferably, the hydrosilylation catalyst is a platinum containing catalyst. A preferred platinum-containing catalyst is a platinum-octanol complex containing 90.9 weight % octyl alcohol and 9.1 weight % chloroplatinic acid.

Another preferred platinum-containing catalyst is a platinum complex formed by reacting chloroplatinic acid containing 4 moles of water of hydration with tetravinylcyclotetrasiloxane in the presence of sodium bicarbonate in an ethanol solution. This catalyst is disclosed in U.S. Pat. No. 3,775,452 to Karstedt, which is hereby incorporated by reference herein.

The catalyst must be used in a catalytic amount, which is that amount sufficient to promote the hydrosilylation reaction. Generally, there must be utilized at least 0.1 part per million of a platinum catalyst, and preferably from 5 ppm to 250 ppm, in terms of parts of platinum metal based on the weight of hydrosilylation mixture. Inhibitors, such as acetylenic alcohols, amines, cyanurates also can be employed when used in an effective amount.

The composition of the present invention may also contain any of the conventional (E) extending and/or (F) reinforcing fillers. The composition contains from about 0 to about 200 and preferably from about 10 to about 100 parts by weight of (E) an extending filler, and from about 0 to about 50, and preferably from about 20 to about 50 parts by weight of (F) a reinforcing filler.

Examples of extending fillers (E) useful herein include alpha quartz, crushed quartz, aluminum oxide, aluminum silicate, zirconium silicate, magnesium oxide, zinc oxide, talc, diatomaceous earth, iron oxide, calcium carbonate, clay, titania, zirconia, mica, glass, such as ground glass or glass fiber, sand, carbon black, graphite barium sulfate, zinc sulfate, wood flour, cork, fluorocarbon polymer powder and the like. The preferred extending filler for use in the present invention is alpha quartz.

Examples of reinforcing fillers (F) include silica, such as fumed silica and precipitated silica; and treated silica fillers such as fumed or precipitated silica that has been reacted with, e.g., an organohalosilane, a disiloxane, or a disilazane. Fumed silica is particularly effective as a reinforcing filler for the silicone component of the present invention. A particularly preferred treated fumed silica is one wherein a fumed silica has been treated first with cyclic polysiloxanes, e.g., dimethylcyclic tetramer, according to the methods known in the art, for example, as taught in U.S. Pat. No. 2,938,009 (Lucas), which is incorporated by reference herein, and then treated with a silazane, e.g., hexamethyldisilazane, for example, as taught in U.S. Pat. No. 3,635,743 (Smith) and U.S. Pat. No. 3,847,848 (Beers), which are both incorporated by reference herein, so as to remove most of the free silanols on the surface of the tetramet treated silica. Such a filler is sometimes referred to herein as "treated fumed silica".

The composition of the present invention can be prepared by homogeneously mixing components (A)–(F) and any optional ingredients, using suitable mixing means, such as a spatula, a drum roller, a mechanical stirrer, a three-roll mill, a sigma blade mixer, a bread dough mixer and a two-roll mill.

The order of mixing components (A)–(F) is not critical, however, it is preferred that components (B) and (C) be brought together in the presence of component (D), most preferable in a final mixing step. Thus, it is possible to mix all components in one mixing step immediately prior to the intended use of the curable composition. Alternatively, certain components can be premixed to form two or more packages which can be stored, if desired, and then mixed in a final step immediately prior to the intended use thereof.

It is preferred to mix components (C), (D), and a portion of component (A), along with certain optional components, such as fillers and solvents, to provide a first package. Separately, component (B), along with the remaining portion of component (A), if any, can be mixed to provide a second package. These two packages can then be stored until the composition of this invention is desired and then homogeneously mixed.

The addition-curable silicone compositions of the invention will directly self-bond in the absence of primer to various plastic, metal, glass, and masonry substrates. Additional plastic substrates to which the composition will bond include plastic substrates selected from polyphenylene/styrene blends, polyacrylamides, polystyrenes, conditioned polycarbonates, polyesters, polyimides, polyetherimides, polybutylene terephthalates, fluoropolymers and non-resin containing polyetherimides. Examples of metal substrates include metal substrates selected from copper, alclad aluminum, anodized aluminum, galvanized steel, cold-rolled steel, cast aluminum, and cast magnesium The thickness of the adhesive composition on a substrate is typically from about 20 to about 60 mils.

The addition-curable compositions of the present invention can be applied onto the surface of the substrate by any suitable means such as rolling, spreading, spraying, and the like, and cured as described above. After application of the adhesive composition onto the substrate, the composition can be cured at a temperature in the range of about 50° C. to 100° C. over a period of about 10 to 30 minutes.

In order that those skilled in the art may better understand the practice of the present invention, the following examples are given by way of illustration and not by way of limitation. All parts are by weight.

Example 1

A mixture of 5.03 g of benzylamine and 23 g of 3-acryloyloxy-1-propyltrimethoxysilane was heated under nitrogen at 40° C. for 24 hours. Complete reaction was shown by $^1$H NMR spectroscopy. Based on method of preparation and $^1$H NMR spectra, the product was,

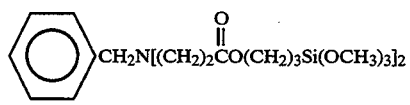

In a Parr® hydrogenation apparatus was placed 4 g of the above reaction product, 20 mls of methanol (dried over 3A sieves) and 1 g of Pd/C (10%, dried at 150° C. for 24 hours). The bottle was pressurized to 40 psi and the mixture shaken for 2 hours at ambient temperatures. The mixture was filtered through Celite® and the methanol removed in vacuo. There was obtained 2.5 g of product. Based on method of preparation and 1H NMR spectroscopy, the product was a bis(-trimethoxysilyltrimethyleneoxycarbonyldimethylene)amine having the formula,

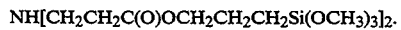

Example 2

A heat addition-curable silicone formulation was prepared by adding 0.23 g of a methylhydrogensiloxydimethylsiloxy copolymer having a hydrogen content of about 0.8% by weight to a mixture of 13 g of mixture of a polydimethylsiloxane having terminal dimethylvinylsiloxy units and a viscosity of about 40,000 centipoise and 20% by weight of the mixture of fumed silica treated with octamethylcyclotetrasiloxane, 10 ppm of platinum in the form of a solution of platinum catalyst shown in Karstedt U.S. Pat. No. 3,775,452, 1.0 μL of 3,5 dimethyl-1-hexyn-3-ol and 0.14 g the above adhesion promoter of example 1.

The mixture was degassed by two cycles of evacuation/centrifugation several Lap Shear 1"×½" samples of metal and thermoplastic were wiped clean with isopropanol. The samples were treated with the above addition-curable formulation. The treated samples were cured at 100° C./1 hour and then tested on an Instron 4202 with a crosshead speed of 0.5 in/min. The following results were obtained, where polycarbonate is Lexan® polycarbonate, polyester is Valox® polyester, and polyetherimide is Ultem® polyetherimide, where all thermoplastics are manufactured by GE Plastics Div.

| Substrate | Failure Mode | Lap Shear Strength (psi) |
| --- | --- | --- |
| Polycarbonate | Cohesive | 390 |
| Polyester | Cohesive | 258 |
| Polyetherimide | Cohesive | 336 |
| Alclad | Cohesive | 300 |
| Steel | Cohesive | 394 |

Adhesive failure resulted when the adhesion promoter was excluded.

Although the above example is directed to only a few of the many variables used in the synthesis of the addition-curable compositions of the present invention and the adhesion promoters used in such compositions, it should be understood that the present invention is directed to a much broader variety of bis(trialkoxysilylalkyleneoxycarbonylalkylene)amine adhesion promoters and addition-curable organopolysiloxane compositions containing such adhesion promoters as shown in the description preceding these examples.

What is claimed is:
1. An addition-curable composition, comprising by weight,
(A) 100 parts of a vinyl-containing polydiorganosiloxane composition comprising:
(1) about 50 to about 100 parts of an essentially cyclic-free vinyl-terminated polydiorganosiloxane having the general formula,

where Vi is a vinyl radical, R is selected from the class consisting of alkyl radicals having 1 to 8 carbon atoms, phenyl radicals, fluoroalkyl radicals having 3 to 10 carbon atoms and mixtures thereof, "m+n" has a value sufficient to provide a polydiorganosiloxane viscosity of 100 to about 100,000 centipoise at 25° C., and a polydiorganosiloxane vinyl content of from about 0.02 to about 2.0 weight %, and
(2) from about 0 to about 50 parts of a solid, benzene-soluble vinyl-containing resin copolymer comprising,

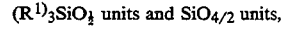

where R$^1$ is a vinyl radical, or a monovalent hydrocarbon radical free of aliphatic unsaturation and containing no more than six carbon atoms, the ratio of (R$^1$)$_3$SiO$_\frac{1}{2}$ units to SiO$_{4/2}$ units being from about 0.5:1 to about 1.5:1, and the resin having a vinyl content of from about 1.5 to about 3.5% by weight,
(B) from about 1 to about 20 parts of a hydrogen-containing polysiloxane having an average unit formula,

where R$^2$ is a monovalent hydrocarbon radical, or halogenated monovalent hydrocarbon radical having from 1 to about 10 carbon atoms and free of aliphatic unsaturation, "a" has a value of from about 0 to about 3, "b" has a value of from about 0 to about 3, and the sum of "a"+"b" has a value of from 0 to 3,
(C) a catalytic amount of a hydrosilylation catalyst,
(D) an amount of a bis(trialkoxysilylalkyleneoxycarbonylalkylene)amine having the formula, $NH[R^3C(O)OR^4Si(OR^5)_3]_2$, which is effective as an adhesion promoter, where $R^3$ and $R^4$ are selected from the same or different $C_{(2-8)}$ alkylene radicals, and $R^5$ is selected from the same or different $C_{(1-4)}$ alkyl radicals, (E) from about 0 to about 200 parts of an extending filler, and (F) from about 0 to about 50 parts of a reinforcing filler, and in the absence of (A)(2), an amount effective for reinforcement.

2. An addition-curable composition in accordance with claim 1, where the vinyl-containing polydiorganopolysiloxane is a vinyl- containing polydimethylsiloxane.

3. An addition-curable composition in accordance with claim 1, where the solid, benzene-soluble vinyl-containing resin comprises a mixture of $(CH_3)_3SiO_{\frac{1}{2}}$ units and $Vi(CH_3)_2SiO_{\frac{1}{2}}$ units and $SiO_2$ units.

4. An addition-curable composition in accordance with claim 1, where the hydrosilylation catalyst is a platinum catalyst.

5. An addition-curable composition in accordance with claim 1, where the adhesion promoter is $NH[CH_2CH_2C(O)OCH_2CH_2CH_2Si(OCH_3)_3]_2$.

6. A bis(trialkoxysilylalkyleneoxycarbonylalkylene)amine having the formula, $NH[R^3C(O)OR^4Si(OR^5)_3]_2$ where $R^3$ and $R^4$ are selected from the same or different $C_{(2-8)}$ alkylene radicals, and $R^5$ is selected from the same or different $C_{(1-4)}$ alkyl radicals.

7. The compound, $NH[CH_2CH_2C(O)OCH_2CH_2CH_2Si(OCH_3)_3]_2$.

* * * * *